United States Patent [19]

Rutherford et al.

[11] 4,036,983
[45] July 19, 1977

[54] FERROCENE COMPOUNDS AND PHARMACEUTICAL COMPOSITION FOR USE IN TREATMENT OF IRON DEFICIENCY IN AN ANIMAL

[75] Inventors: David Rutherford, Loughborough; Peter Williams, Holmes Chapel; Richard Anthony Raphael, Loughborough, all of England

[73] Assignee: Fisons Limited, London, England

[21] Appl. No.: 647,133

[22] Filed: Jan. 7, 1976

[30] Foreign Application Priority Data

Jan. 15, 1975 United Kingdom ............... 1682/75

[51] Int. Cl.² .................................................. A01N 9/00
[52] U.S. Cl. .............................. 424/295; 260/439 CY
[58] Field of Search ................ 260/439 CY; 424/295

[56] References Cited

U.S. PATENT DOCUMENTS

| | | | |
|---|---|---|---|
| 3,035,978 | 5/1962 | Jones et al. | 260/439 CY X |
| 3,064,026 | 11/1962 | Rausch | 260/439 CY |
| 3,382,267 | 5/1968 | Suh | 260/439 CY |
| 3,952,036 | 4/1976 | Suh | 260/439 CY |

*Primary Examiner*—Helen M. S. Sneed

*Attorney, Agent, or Firm*—Merriam, Marshall, Shapiro & Klose

[57] ABSTRACT

These are described compounds of formula I,

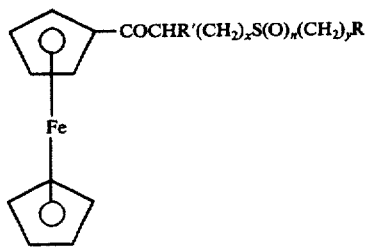

in which R is a cycloalkyl group,
n is 0, 1 or 2,
R' is hydrogen, phenyl, alkyl C 1 to 6, cycloalkyl C 4 to 6, alkyl-cycloalkyl C 5 to 8, or phenyl-(alkyl C 1 to 6),
x is a whole number from 0 to 8, and
y is a whole number from 0 to 5.

There are also described processes for making the compounds and pharmaceutical, e.g. haematinic, compositions containing the compounds.

14 Claims, No Drawings

FERROCENE COMPOUNDS AND PHARMACEUTICAL COMPOSITION FOR USE IN TREATMENT OF IRON DEFICIENCY IN AN ANIMAL

This invention relates to new compounds, methods for their preparation and compositions containing them.

According to our invention we provide compounds of formula I,

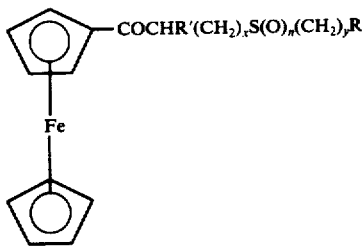

in which R is a cycloalkyl group,
  $n$ is 0, 1 or 2,
  R' is hydrogen, phenyl, alkyl C 1 to 6, cycloalkyl C 4 to 6, alkyl-cycloalkyl C 5 to 8, or phenyl-(alkyl C 1 to 6),
  $x$ is a whole number from 0 to 8, and
  $y$ is a whole number from 0 to 5.

According to our invention we also provide a process for the production of a compound of formula I, which comprises
  a. producing a compound of formula I in which $n$ is 0, by
    (i) reacting a compound of formula II,

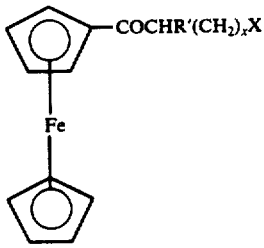

in which R' and $x$ are as defined above, and
  X is a good leaving group, or a group —SM, with a compound of formula III,

in which
  R and $y$ are as defined above,
  Z is a group —SM when X is a good leaving group, or Z is a good leaving group when X is a group —SM, and
  M is hydrogen or an alkali metal,
  ii. reacting ferrocene with a compound of formula IV,

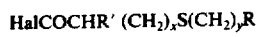

in which
  R, R', $y$ and $x$ are as defined above, and
  Hal represents a halogen atom, iii. reacting a compound of formula II in which X is a group —SH, with an appropriate cycloalkene, or iv. producing a compound of formula I in which $x$ is a whole number from 1 to 8, by reacting a compound of formula V,

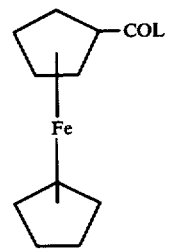

in which L is a group —CR'=CH$_2$ or a group —CHR'(CH$_2$)$_z$CH=CH$_2$, in which R' is as defined above, and $z$ is a whole number from 0 to 6, with a compound of formula III in which Z is a group —SH, b. producing a compound of formula I in which $n$ is 1 or 2,
  by selective oxidation of a compound of formula I in which $n$ is 0, or c. producing a compound of formula I in which R' is alkyl C 1 to 6, by reacting a corresponding compound of formula I in which R' is hydrogen, with a compound RzX in which X is as defined above and Rz is an alkyl C 1 to 6 group.

Process (a) (i) may be carried out in a suitable solvent system, e.g. a mixture of dioxan and water, and at a temperature of from about 20° to 120°to C. The good leaving group, e.g. X, may be, for example, an anion forming group, e.g. a halogen atom such as a bromine or iodine, or preferably a chlorine atom, or may be an organic sulphonate group, e.g. a methane sulphonate or a p-toluene sulphonate group. We prefer to use an alkali metal salt, e.g. a sodium salt, as the compound of formula II or III, or to carry out the reaction in the presence of a base, e.g. sodium hydroxide.

Process (a) (ii) may be carried out in a solvent which is inert under the reaction conditions, for example methylene chloride. The reaction is preferably carried out under Friedel-Crafts reaction conditions, for example in the presence of a Lewis acid such as aluminium chloride. The reaction is preferably carried out at a temperature of from about −25° to 45° C.

Processes (a) (iii) and (a) (iv) may be carried out in the absence of a solvent, or in a solvent which is inert under the reaction conditions, e.g. ethanol, carbon tetrachloride, dioxan or a mixture of dioxan and water. The reactions may, if desired, be carried out in the presence of a catalyst, e.g. piperidine or sodium ethoxide. The reactions may be carried out at a temperature of from about 0° C to the boiling point of the solvent used, e.g. about 100° C.

In process (b) the oxidation may be carried out in a solvent which is inert under the reaction conditions, e.g. chloroform. When a compound in which $n$ is 1 is required, equimolar proportions of the compound of formula I in which $n$ is 0 and of the oxidising agent may be used. When a compound in which $n$ is 2 is desired, two or more moles of oxidising agent should be used for each mole of the compound of formula I in which $n$ is 0.

Oxidising agents suitable for use in this reaction include hydrogen peroxide and organic per acids containing a —CO$_3$H group, e.g. m-chloroperbenzoic acid.

The reaction of process (c) is preferably carried out in the presence of a non-nucleophilic proton abstracting agent, for example an alkali metal hydride such as lithium or preferably sodium hydride. The reaction is also preferably carried out in a suitable, preferably polar, solvent such as the dimethyl ether of ethylene glycol. The reaction is preferably carried out at an elevated temperature, e.g. at the boiling point of the reaction mixture.

The compounds of formula I may be separated from reaction mixtures containing them using conventional techniques.

The compounds of formula II in which X is a chlorine atom are for the most part known. The other compounds of formula II may be made inter alia by methods analogous to those known for the preparation of similar known compounds, or by replacement reactions involving replacement of the chlorine atom in a chloroalkanoylferrocene, e.g. by reacting chloroacetylferrocene with sodium bromide or sodium iodide to form bromoacetylferrocene or iodoacetylferrocene respectively.

The compounds of formulae III, IV and V are either known or may be made by methods analogous to those known for the preparation of the known compounds. Thus compounds of formula IV may be made by reacting a corresponding alkyl- or cycloalkyl alkylthioether with lithium and reaction of the resulting product with CO$_2$ and water to give the corresponding cycloalkyl-thioalkanoic acid, (JACS, 1946, 62, 987) which is then reacted with thionyl chloride to yield the compound of formula IV. The cycloalkyl-thioalkanoic acid may also be produced by reacting a corresponding cycloalkyl-thiol with a haloalkanoic acid or an alkali metal salt thereof.

The compounds of formula I are useful because they possess pharmacological activity in animals. In particular, the compounds are useful as haematinics (as is shown by the rapid correction of iron deficiency anaemia, as determined by following haemoglobin regeneration, in anaemic rats to which the compounds have been administered orally: Lawrence and Bacharach, Evaluation of Drug Activities - Pharmacometrics, Academic Press, New York 1964 page 563) and are indicated for use in the treatment of iron deficiency in man and other animals, e.g. pigs, horses and cattle. The compounds are particularly indicated for the treatment of iron deficiency anaemia in women. A substantial proportion of the dose administered to rats is transformed into physiologically acceptable iron stores (ferritin) and is retained in organs such as the liver. The degree of storage may be determined by measuring the non-haem iron in the liver by the method of Torrance and Bothwell - South African Journal of Medical Science 1962 Volume 32 page 9. The compounds are particularly indicated for oral administration.

For the above mentioned use, the dosage administered will, of course, vary depending upon the compound employed, mode of administration and treatment desired. However in general, satisfactory results are obtained when the compound is administered orally at a daily dosage of from about 1 milligram to 250 milligrams active ingredient per kilogram of animal body weight, preferably given 1 to 3 times a day, or in sustained release form. For man the total daily dosage is in the range of from about 50 milligrams to about 2,000 milligrams active ingredient, and unit dosage forms suitable for oral or parenteral administration comprise from about 20 to about 2,000 milligrams of the active ingredient.

The compounds according to the invention may be formulated into pharmaceutical compositions with pharmaceutically acceptable adjuvants, carriers or diluents. The nature of the adjuvant, carrier or diluent will depend in part on the intended mode of administration of the composition. Examples of suitable adjuvants, carriers and diluents are: for tablets and dragees — lactose, starch, talc, stearic acid or an effervescent couple; for capsules — tartaric acid or lactose; for orally administered solutions or suspensions and for injectable solutions - water, alcohols, glycerin or vegetable oils; and for suppositories - natural or hardened oils or waxes. The compounds may also be formulated as a paste, granule, chewable gum or tablet, jelly, drinkable ampule, and/or in combination with a human or animal feedstuff, e.g. bread. In addition, the compositions may also include other pharmacologically active components such as Vitamin B12, folic acid, Vitamin C (and-/or other vitamins), an analgesic, e.g. aspirin, an anthelmintic or an oral contraceptive. The composition may also contain suitable preserving, stabilising and wetting agents, solubilisers and sweetening and colouring agents and flavourings. If desired, the composition may be formulated in sustained release form or in enteric coated form. Compositions for oral administration are preferred. We prefer to use the compound of formula I in a solid particulate form having a mass median diameter of less than 10, and preferably less than 5 microns.

The compounds of this invention possess pharmacological properties of an order not demonstrated by similar known compounds.

R may be a cyclobutyl, cycloheptyl, or preferably a cyclopentyl or cyclohexyl group. We prefer those compounds in which R' is hydrogen, or ethyl but other values which may be mentioned are cyclohexyl, phenyl, benzyl and cyclohexylmethyl. We also prefer x to be 0, 1, 2 or 3, n to be 0 or 1 and y to be 0.

The invention is illustrated, but in no way limited by the following Examples in which the temperatures are in degrees centigrade.

EXAMPLE 1

3-(Cyclohexylthio)propionyl ferrocene a. 3-Chloropropionyl ferrocene

A solution of ferrocene (2.63 kg, 14.2 mole) and 3-chloropropionyl chloride (1.8 kg, 15.6 moles) in dry dichloromethane (23.5 l) was cooled to −3° and treated over 1 hour with aluminium chloride (2.08 kg, 15.6 mole). The reaction mixture was left to stir for 2 hours. To this was then added ice water (30 kg) and the two layers separated. The aqueous layer was washed with dichloromethane and the combined organic liquors were washed with water (30 l), 2% aqueous sodium bicarbonate solution (20 l) and water again (60 l). The organic liquors were then dried and concentrated affording black/brown semi-solid chloropropionyl ferrocene (3.5 kg).

This product was used in crude form in step (b) below. For analytical purposes it was chromatographed on silica gel using chloroform as eluent. This afforded an oil which crystallised on standing giving a solid, mp 62°–63°.

b. 3-(Cyclohexylthio)propionyl ferrocene

Sodium hydroxide (0.25 mole) dissolved in minium water was treated with cyclohexylmercaptan (0.25 mole) and 700 ml dioxan. Chloropropionylferrocene (0.25 mole) was then added and the resulting mixture stirred on a steam bath for 3 hours. The mixture was diluted with water and extracted with chloroform. The organic liquors were washed successively with aqueous sodium hydroxide and water, dried and concentrated affording crude product. This was chromatographed through a silica gel column (20:1 ratio of silica to substrate) using initially 1% ethyl acetate/petroleum ether (60°-80°) then 3% ethyl acetate/petroleum ether as eluent. This afforded an oil which crystallised on cooling and trituration with petroleum ether. The solid was filtered off and washed with petroleum ether affording 3-(cyclohexylthio)propionyl ferrocene, mp 46.5°–48.5°, in 20% yield. Concentration of the petroleum ether liquors afforded a further 3% yield of product.

EXAMPLE 2

2-(Cyclohexylthio)butyrylferrocene a. 2-Bromobutyrylferrocene

Thionyl chloride (11.9g, 0.1M) was added to a stirred solution of 2-bromobutyric acid (16.7g, 0.1M) in dry toluene (100 ml) and the mixture was heated under reflux for 24 hours. Additional thionyl chloride (11.9g, 0.1M) was added and heating under reflux was continued for a further 2 hours. Volatile materials were then removed by rotary evaporation. The resulting oil was added to a stirred solution of ferrocene (18.6g, 0.1M) in dry methylene chloride (200 ml) at 0°-5°, followed by aluminium chloride (13.3g, 0.1M) in small portions. After stirring at 0°-5° for a further 30 minutes, the mixture was poured onto ice water. The organic layer was separated, washed with water, dried over anhydrous magnesium sulphate and finally evaporated to yield a sticky solid. 2-Bromobutyrylferrocene was obtained as a red oil by subjecting the product to column chromatography on silica gel with chloroform as the eluent.

b. 2-(Cyclohexylthio)butyrylferrocene

Cyclohexylmercapton (0.6g, 0.005M) was added to a solution of sodium hydroxide (0.2g, 0.005M) in water (ca 0.5 ml). Dioxan (20 ml) was introduced and the resulting white precipitate was dissolved by adding water dropwise. After 2-bromobutyrylferrocene (1.6g, 0.005M) had been added, the reaction mixture was heated on a steam bath for 30 minutes, after which time thin layer chromatography indicated that the reaction was complete. Water was subsequently added to the cooled reaction mixture which was then treated with chloroform. The organic layer was separated, washed with dilute sodium hydroxide solution, water and finally dried over magnesium sulphate before evaporation. The red oil (0.80g) obtained was purified by column chromatography on silica gel with chloroform as the eluant to yield the title compound as orange needles (0.43g) mp = 56°-8°.

EXAMPLE 3

Cyclohexylsulphinylpropionylferrocene 3-(Cyclohexylthio)propionylferrocene (1.3g, 0.00366M) was dissolved in chloroform (30 ml) and the solution was cooled in ice/water. m-Chlorobenzoic acid (0.63g, 0.00366M) was then added slowly with stirring. Following the addition, stirring was continued at room temperature for 3 hours, and the resulting solution was washed with dilute sodium bicarbonate solution and water, before being dried over anhydrous sodium sulphate. Removal of the solvent on a rotary evaporator yielded a red oil which subsequently crystallised as orange needles of the title compound (1.15g) mp = 90°-1°.

EXAMPLE 4

Cyclohexylthioacetylferrocene

Cyclohexylmercaptan (11.6g, 0.1M) was added to a solution of sodium hydroxide (4g, 0.1M) in water (20 ml). Dioxan (300 ml) was added and the resulting white precipitate was redissolved on the addition of a further small quantity of water. Chloroacetylferrocene (27.3g, 0.1M) was then added and the reaction mixture was heated at 100° for 2 hours with stirring. The cooled reaction mixture was diluted with water and extracted with chloroform. The organic layer was washed with water, dried over anhydrous sodium sulphate and concentrated by rotary evaporation. The crystalline product obtained was purified by recrystallisation from petroleum ether (40-60), but needed column chromatography on silica gel with petroleum ether (60-80)-ethyl acetate (9:1) for final purification. Orange needles of the title compound were thus obtained (6.4g) mp = 89°.

EXAMPLE 5

Cyclopentylthioacetylferrocene

Cyclopentylmercaptan (ca 1.5g, 0.015M) was added to a solution of sodium hydroxide (0.6g, 0.015M) in water (3 ml). Dioxan (45 ml) was added, followed by chloroacetylferrocene (3.9g, 0.015M), and the mixture was heated at 100° for 2 hours with stirring. On cooling, water was added to the reaction mixture which was then extracted with chloroform. The organic layer was washed with dilute sodium hydroxide and water before it was dried over anhydrous magnesium sulphate and evaporated to an oil on a rotary evaporator. The product was isolated after column chromatography on silica gel using gradient elution with 1-2½% (v/v) ethyl acetate in petroleum ether (60-80). Orange needles (0.40g) of the title compound were obtained mp = 78°-9°.

EXAMPLE 6

3-(Cyclohexylthio)propionyl ferrocene

A solution of acryloyl ferrocene (2.16g) and cyclohexylmercaptan (1.16g) in ethanol (50 ml) was set aside at ambient temperature for 24 hours. Evaporation of the ethanol gave an oil which was dissolved in chloroform (100 ml). The chloroform solution was washed successively with aqueous sodium hydroxide and water, dried over sodium sulphate and evaporated affording crude product. This was chromatographed through a silica-gel column (66g) using initially 1% ethyl acetate/petroleum ether (60°-80°) then 3% ethyl acetate/petroleum ether as eluent. This afforded an oil which crystallised on cooling and trituration with petroleum ether. The solid was filtered off, washed well with petroleum ether and dried giving the title compound, m.p. 46.5°-48.5°to C.

EXAMPLE 7

The following compounds may be made by the processes described above:

3-(Cyclobutylthio)propionyl ferrocene
3-(Cycloheptylthio)propionyl ferrocene
3-(Cyclohexylmethylthio)propionyl ferrocene 3-(Cyclohexylthio)butyryl ferrocene
2-(Cyclohexylthio)phenylpropionyl ferrocene.

We Claim:

1. A compound of formula I,

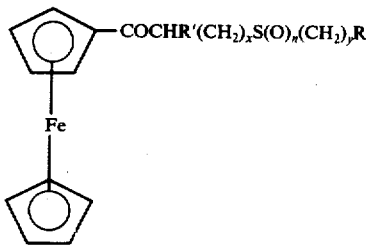

in which
R is a cycloalkyl group,
$n$ is 0, 1 or 2,
R' is hydrogen, phenyl, alkyl C 1 to 6, cycloalkyl C 4 to 6, alkyl-cycloalkyl C 5 to 8, or phenyl-(alkyl C 1 to 6),
$x$ is a whole number from 0 to 8, and
$y$ is a whole number from 0 to 5.

2. A compound according to claim 1, wherein R, $n$, $x$ and $y$ are as defined in claim 1, and R' is hydrogen, phenyl, alkyl C 1 to 6, cycloalkyl C 4 to 6 or alkyl-cycloalkyl C 5 to 8.

3. A compound according to claim 1, wherein R is cyclopentyl or cyclohexyl.

4. A compound according to claim 1, wherein R' is hydrogen, ethyl, cyclohexyl, phenyl, benzyl or cyclohexylmethyl.

5. A compound according to claim 4, wherein R' is hydrogen.

6. A compound according to claim 1, wherein $x$ is 0, 1, 2 or 3.

7. A compound according to claim 6, wherein $n$ is 0 or 1.

8. A compound according to claim 7, wherein $y$ is 0.

9. A compound according to claim 1, which is 3-(Cyclohexylthio)propionyl ferrocene.

10. A compound according to claim 1 and selected from
2-(cyclohexylthio)butyrylferrocene,
cyclohexylsulphinylpropionylferrocene,
cyclohexylthioacetylferrocene,
cyclopentylthioacetylferrocene,
3-(cyclobutylthio)propionylferrocene,
3-(cycloheptylthio)propionylferrocene,
3-(cyclohexylmethylthio)propionylferrocene,
3-(cyclohexylthio)butyrylferrocene, and
2-(cyclohexylthio)phenylpropionylferrocene.

11. A compound according to claim 1 in a solid particulate form having a mass median diameter of less than 10 microns.

12. A pharmaceutical composition for use in treatment of iron deficiency in an animal comprising a therapeutically effective amount of a compound according to claim 1, as active ingredient, in combination with a pharmaceutically acceptable adjuvant, diluent or carrier.

13. A composition according to claim 12, comprising from 20 to 2,000 mg of active ingredient in unit dosage form.

14. A method of treating iron deficiency in an animal, which comprises administering an effective quantity of a compound according to claim 1 to an animal suffering from iron deficiency.

* * * * *